(12) United States Patent
Jeon et al.

(10) Patent No.: US 12,377,282 B2
(45) Date of Patent: Aug. 5, 2025

(54) APPARATUS FOR MICROWAVE HEAT SPREAD AND AN OPERATION METHOD THEREOF

(71) Applicant: ELECTRONICS AND TELECOMMUNICATIONS RESEARCH INSTITUTE, Daejeon (KR)

(72) Inventors: Soon Ik Jeon, Daejeon (KR); Kwang Jae Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 482 days.

(21) Appl. No.: 17/718,118

(22) Filed: Apr. 11, 2022

(65) Prior Publication Data

US 2022/0331604 A1   Oct. 20, 2022

(30) Foreign Application Priority Data

Apr. 19, 2021   (KR) .......................... 10-2021-0050686

(51) Int. Cl.
   *A61N 5/02*   (2006.01)
   *H05B 6/80*   (2006.01)

(52) U.S. Cl.
   CPC ............... *A61N 5/025* (2013.01); *H05B 6/80* (2013.01)

(58) Field of Classification Search
   CPC .................................................... A61N 5/025
   See application file for complete search history.

(56) References Cited

U.S. PATENT DOCUMENTS

| | | | |
|---|---|---|---|
| 5,039,995 | A | 8/1991 | Hulbert |
| 5,503,150 | A | 4/1996 | Evans |
| 6,470,217 | B1 | 10/2002 | Fenn et al. |
| 10,492,731 | B2 | 12/2019 | Son et al. |
| 2007/0244530 | A1 | 10/2007 | Ren |
| 2010/0010335 | A1 | 1/2010 | Kim et al. |
| 2016/0287086 | A1* | 10/2016 | Son ..................... A61B 5/0093 |
| 2018/0264281 | A1* | 9/2018 | Kim ..................... A61N 5/025 |
| 2019/0111275 | A1* | 4/2019 | Jeon ..................... H05B 6/664 |
| 2020/0139150 | A1 | 5/2020 | Jeon et al. |

FOREIGN PATENT DOCUMENTS

| | | |
|---|---|---|
| KR | 1019890009018 A | 7/1989 |
| KR | 1020160118919 A | 10/2016 |
| KR | 1020190042431 A | 4/2019 |

* cited by examiner

*Primary Examiner* — Kaitlyn E Smith
(74) *Attorney, Agent, or Firm* — Rabin & Berdo, P.C.

(57) ABSTRACT

A microwave heat spread apparatus and an operating method thereof are provided. The microwave heat spread apparatus includes: a plurality of antennas respectively disposed at a plurality of positions of the human body and radiating microwaves into the human body; a plurality of channel transceivers respectively connected to the plurality of antennas and configured to transmit and receive the microwaves through a corresponding antenna; a transmission signal distributor configured to distribute a signal to each of the plurality of channel transceivers; a controller configured to control transmission and reception of signals through the channel transceivers; and a detector configured to detect a difference between a signal received through a channel transceiver after passing through the human body and a signal before passing through the human body.

9 Claims, 8 Drawing Sheets

APPARATUS FOR MICROWAVE HEAT SPREAD AND AN OPERATION METHOD THEREOF

CROSS-REFERENCE TO RELATED APPLICATION

This application claims priority to and the benefit of Korean Patent Application No. 10-2021-0050686 filed in the Korean Intellectual Property Office on Apr. 19, 2021, the entire contents of which are incorporated herein by reference.

BACKGROUND OF THE INVENTION

(a) Field of the Invention

The present disclosure relates to a heat spread apparatus, and more particularly, to a microwave heat spread apparatus and an operating method thereof.

(b) Description of the Related Art

Treatment of diseases such as pain diseases and degenerative musculoskeletal diseases has been mainly treated with surgery, but due to side effects such as pain of the patient and relapse, non-invasive treatment that converts and treats energy such as microwaves from outside the human body into heat has been recently used. As a technology related to non-invasive treatment, there is a technology of propagating microwaves into the body with two antennas, generating heat in a lesion, and controlling heat by inserting a sensor for temperature monitoring into the body.

However, these technologies have the problem of not being able to evenly distribute the heat from the surface to the deep part when pain or inflammation occurring in a wide range of areas of the body is alleviated or needs healing and the problem of accompanying patient's suffering due to the insertion of a sensor to monitor and maintain the temperature and the like.

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide an apparatus and a method for generating heat in the human body through microwaves, uniformly distributing and spreading the heat, and detecting the temperature change in the human body non-invasively to prevent the risk of high heat in advance.

An exemplary embodiment of the present invention provides an apparatus for spreading microwave heat into a human body. The apparatus includes: a plurality of antennas respectively disposed at a plurality of positions of the human body and radiating microwaves into the human body; a plurality of channel transceivers respectively connected to the plurality of antennas and configured to transmit and receive the microwaves through a corresponding antenna; a transmission signal distributor configured to distribute a signal to each of the plurality of channel transceivers; a controller configured to control transmission and reception of signals through the channel transceivers; and a detector configured to detect a difference between a signal received through a channel transceiver after passing through the human body and a signal before passing through the human body, wherein in a state in which one channel transceiver of the plurality of channel transceivers operates in a transmission state and at least one of the remaining channel transceivers operates in a reception state, the controller estimates an amount of temperature change based on the difference output from the detector and controls the channel transceivers according to the estimated amount of temperature change.

In an implementation, the controller may be configured to estimate an amount of temperature change in the human body based on the difference, control the plurality of channel transceivers to stop a microwave heat generating operation for radiating microwaves through the plurality of antennas when the estimated amount of temperature change exceeds a predetermined threshold, and control the plurality of channel transceivers to continue the microwave heat generating operation when the estimated amount of temperature does not exceed the predetermined threshold.

In an implementation, for each of the plurality of channel transceivers, the estimating of an amount of temperature change may be performed while a corresponding channel transceiver operates in a transmission state and at least one of remaining channel transceivers operates in a reception state.

In an implementation, the controller may be configured to perform first control of controlling all of the plurality of channel transceivers to be in a transmission state so that a microwave heat generating operation in which microwaves are radiated through all of the antennas respectively connected to the plurality of channel transceivers is performed, and when a predetermined time elapses after performing the first control, perform second control of controlling one channel transceiver among the plurality of channel transceivers to be in a transmission state and controlling at least one of the remaining channel transceivers to be in a reception state.

In an implementation, the controller may be configured to repeatedly perform the second control while operating each of the plurality of channel transceivers in a transmission state, and perform an operation of estimating an amount of temperature change based on the difference from the detector and comparing the estimated amount of temperature change with a predetermined threshold whenever the second control is performed.

In an implementation, the detector may use a signal provided from the transmission signal distributor as the signal before passing through the human body. In this case, the detector may include: a first detector configured to detect an intensity difference between an intensity of a signal received through the channel transceiver and an intensity of a signal provided from the transmission signal distributor; and a second detector configured to detect a phase difference between a phase of a signal received through the channel transceiver and a phase of a signal provided from the transmission signal distributor, wherein the controller may be configured to estimate the amount of temperature change in the human body based on the intensity difference and the phase difference.

In an implementation, each of the plurality of channel transceivers may include: a transmitting switch; a circulator configured to send a signal from the transmitting switch to a corresponding antenna so that microwave radiation is performed or to output a signal received from the corresponding antenna; and a receiving switch connected to an output terminal of the circulator and configured to be turned on/off according to a control signal applied from the controller to send the received signal output from the circulator to the detector, wherein a transmission operation may be performed through the corresponding antenna according to on/off of the transmitting switch, and a reception operation is performed through the corresponding antenna according to on/off of the receiving switch.

In an implementation, each of the plurality of channel transceivers may include: a microwave intensity and phase controller configured to adjust an intensity and phase of a signal provided from the transmission signal distributor according to values of intensity and phase provided from the controller and output to the transmitting switch; a transmission amplifier configured to amplify a signal applied through the transmitting switch and send it to the circulator; and a reception amplifier configured to amplify a signal applied through the receiving switch and send it to the detector.

In an implementation, the apparatus may further include: a reception channel selector connected to an output terminal of the plurality of channel transceivers and configured to select a single channel transceiver; and a reception signal distributor connected to an output terminal of the reception channel selector to transmit a signal output from the reception channel selector to the detector.

In an implementation, each of the plurality of antennas may be an antenna attached to the human body via a cable, and the apparatus operates as a non-invasive microwave hyperthermia apparatus.

Another embodiment of the present invention provides a method of operating an apparatus that spreads microwave heat into a human body. The method includes: performing, by the apparatus, a microwave heat generating operation of radiating microwaves into the human body by operating all of a plurality of antennas respectively disposed at a plurality of positions of the human body to be in a transmission state; performing, by the apparatus, a temperature change amount detection operation when a predetermined time elapses after performing the microwave heat generating operation; comparing, by the apparatus, an amount of temperature change in the human body estimated by the temperature change amount detection operation with a predetermined threshold; and stopping, by the apparatus, the microwave heat generating operation of radiating microwaves when the estimated amount of temperature change exceeds a predetermined threshold value and continuing the microwave heat generating operation when the estimated amount of temperature does not exceed the predetermined threshold.

In an implementation, the performing of a temperature change amount detection operation may include controlling one channel transceiver among the plurality of channel transceivers to be in a transmission state and at least one of remaining channel transceivers to operate in a reception state, and then performing a temperature change amount detection operation by using a signal received by a channel transceiver in the reception state.

In an implementation, the performing of a temperature change amount detection operation may include: detecting an intensity difference between an intensity of the signal received by the channel transceiver in the reception state after passing through the human body and an intensity of a signal applied to the channel transceiver in the transmission state; detecting a phase difference between a phase of the signal received by the channel transceiver in the reception state and a phase of the signal applied to the channel transceiver in the transmission state; and estimating the amount of temperature change in the human body based on the intensity difference and the phase difference.

In an implementation, for each of the plurality of channel transceivers, the performing of a temperature change amount detection operation and the comparing of an amount of temperature change may be repeatedly performed whenever each of the plurality of channel transceivers is set to be in a transmission state.

In an implementation, the continuing of the microwave heat generating operation may include, after the performing of a temperature change amount detection operation and the comparing of an amount of temperature change are performed for all of the plurality of channel transceivers, when the estimated amount of temperature does not exceed the predetermined threshold for all of the plurality of channel transceivers, controlling all of the plurality of channel transceivers to be in a transmission state to perform the microwave heat generating operation.

DETAILED DESCRIPTION OF THE EMBODIMENTS

In the following detailed description, only certain exemplary embodiments of the present disclosure have been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. Like reference numerals designate like elements throughout the specification.

Throughout the specification, unless explicitly described to the contrary, the word "comprise", and variations such as "comprises" or "comprising", will be understood to imply the inclusion of stated elements but not the exclusion of any other elements.

The expressions described in the singular may be interpreted as singular or plural unless an explicit expression such as "one", "single", and the like is used.

In addition, terms including ordinal numbers such as "first" and "second" used in embodiments of the present disclosure may be used to describe components, but the components should not be limited by the terms. The terms are only used to distinguish one component from another. For example, without departing from the scope of the present disclosure, a first component may be referred to as a second component, and similarly, the second component may be referred to as the first component.

Hereinafter, a microwave heat spread apparatus and an operating method thereof according to an embodiment of the present disclosure will be described with reference to the drawings.

The intensity and phase of radio waves (e.g., microwaves) passing through a medium change according to a change in the permittivity of the medium, and the change in permittivity occurs due to a change in the temperature of the medium. Therefore, by measuring the change in the intensity and phase of microwaves passing through the medium, the amount of temperature change in the propagation path inside the medium can be estimated. An embodiment of the present disclosure provides an apparatus for generating heat by microwaves and spreading this heat to be uniformly distributed, and in particular, provides an apparatus for detecting changes in body temperature non-invasively based on changes in the intensity and phase of microwaves passing through body tissues and regulating heat based on a detected change in body temperature.

Figure 1:
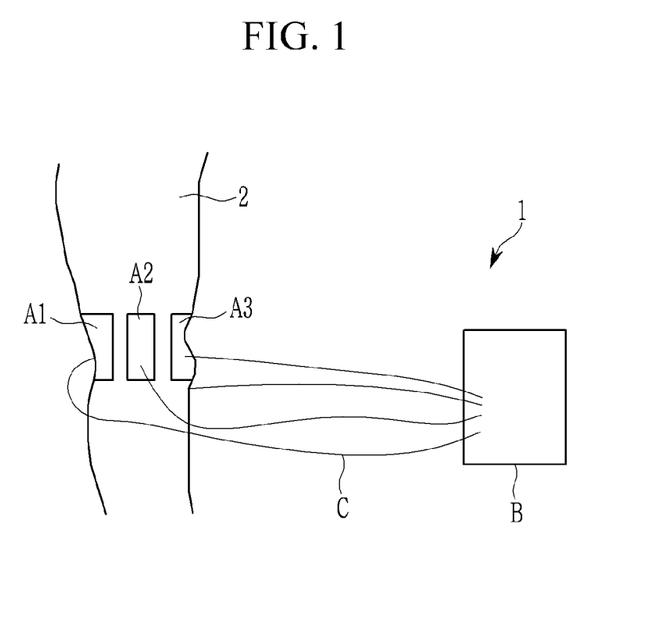
FIG. 1 is a diagram illustrating a concept to which a microwave heat spread apparatus according to an embodiment of the present disclosure is applied.

FIG. 1 is a diagram illustrating a concept to which a microwave heat spread apparatus according to an embodiment of the present disclosure is applied.

Here, the description will be given by taking as an example that the apparatus according to an embodiment of the present disclosure is applied to a microwave hyperthermia apparatus for thermotherapy, but is not limited thereto.

As shown in the accompanying FIG. 1, the microwave heat spread apparatus 1 according to the embodiment of the present disclosure functions as a microwave hyperthermia apparatus applied to the human body, and in this case, includes a plurality of antennas A1 to A3 that are connected from a main body B through a cable C. Here, each of the antennas A1 to A3 is connected to the main body B through each cable C. Each of the antennas A1 to A3 may be implemented in the form of a patch antenna attached to skin of a human body 2.

Each of the antennas A1 to A3 may be attached to a predetermined position of the human body 2, for example, an affected part, as in FIG. 1. The main body B transmits a signal to the antennas A1 to A3 through the cable C, and accordingly, the antennas A1 to A3 radiate radio waves, that is, microwaves, into the human body including the affected part to generate heat in the human body and spread heat evenly throughout the human body. Through this process, diseases such as pain diseases and degenerative musculoskeletal diseases can be treated non-invasively through heat for a certain period of time.

At a predetermined time point, only one antenna (e.g., A1) attached to the skin of the human body 2 through one cable C from the main body B is operated to transmit, i.e., radiate, microwaves into the body, and the remaining antennas (e.g., A2 to A3) are operated to perform a reception operation, that is, to receive a microwave that has passed through the human body. The microwave received through the remaining antennas is transmitted to the main body B through the cable C, and then the process of detecting the difference by comparing the intensity and phase of the microwave received in the main body B with the intensity and phase of the microwave previously received is performed. This process is performed for each microwave received from each antenna that has performed a reception operation. The detection operation may be periodically and repeatedly performed, and the above detection operation may be repeatedly performed while changing the antenna performing the transmission operation among the plurality of antennas A1 to A3.

The amount of change in body temperature is estimated based on the intensity difference and phase difference of microwaves obtained according to the detection operation, that is, the amount of change in body temperature is estimated from the change in the detected values according to the change in human body heat, and the estimated amount of change in body temperature is compared to a threshold predetermined in advance. When the amount of change in body temperature exceeds the threshold, the microwave heat generating operation is stopped, and when the amount of change in body temperature is lower than the threshold, the microwave heat generating operation is continued.

Next, a detailed structure of a microwave heat spread apparatus according to an embodiment of the present disclosure that operates based on this concept will be described.

Figure 2:
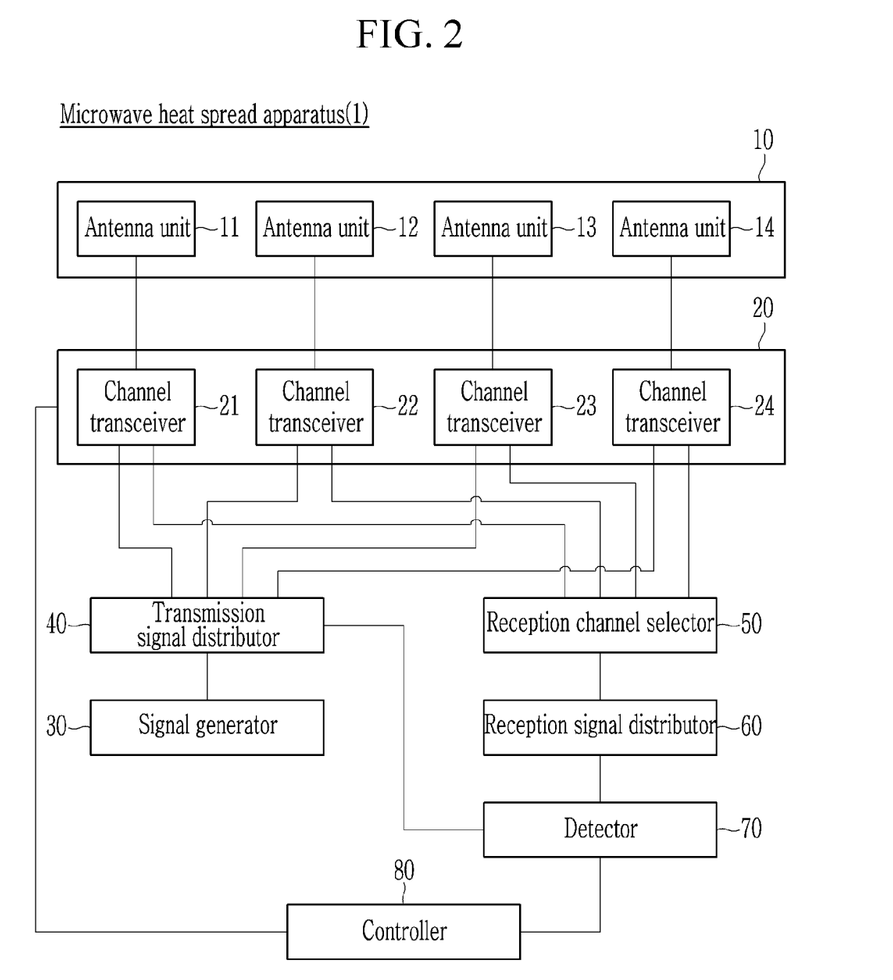
FIG. 2 is a block structural diagram of a microwave heat spread apparatus according to an embodiment of the present disclosure.
Figure 3:
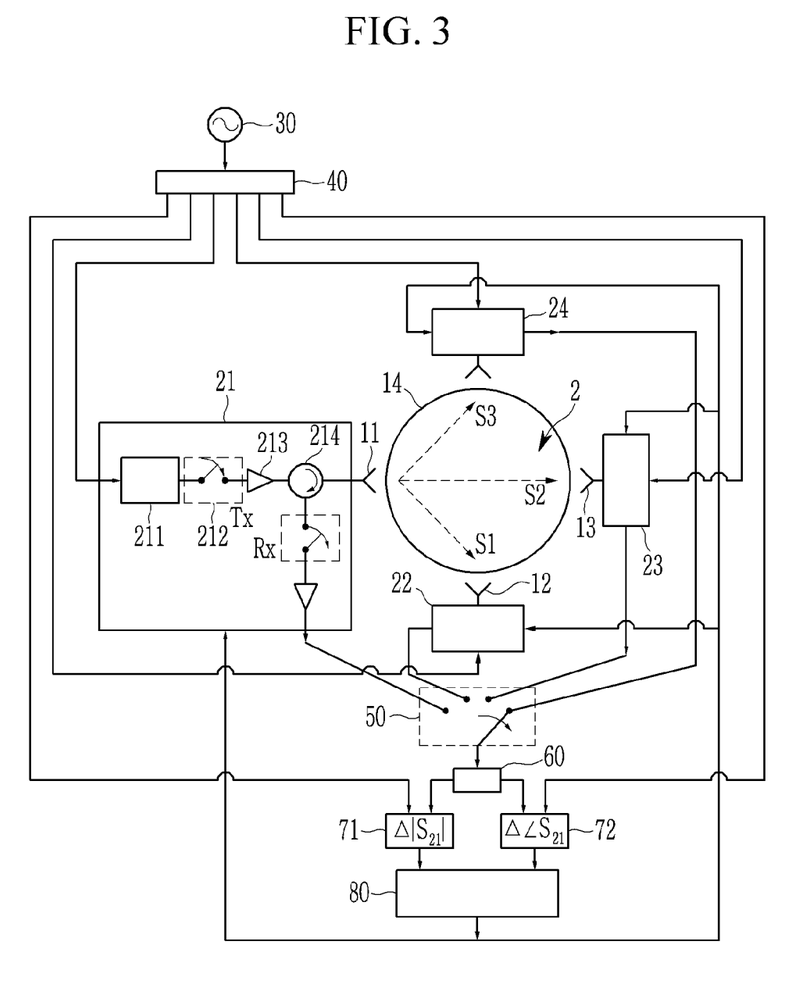
FIG. 3 is a detailed circuit diagram of a microwave heat spread apparatus according to an embodiment of the present disclosure.

FIG. 2 is a block structural diagram of a microwave heat spread apparatus according to an embodiment of the present disclosure, and FIG. 3 is a detailed circuit diagram of the microwave heat spread apparatus according to an embodiment of the present disclosure.

As shown in FIG. 2, the microwave heat spread apparatus 1 according to an embodiment of the present disclosure includes an antenna unit 10, a channel transceiver 20, a signal generator 30, a transmission signal distributor 40, a reception channel selector 50, a reception signal distributor 60, a detector 70, and a controller 80.

The antenna unit 10 includes a plurality of antennas, and each antenna may be a patch-type antenna. Here, for convenience of description, four antennas 11 to 14 will be described as an example, and the present disclosure is not limited thereto.

The channel transceiver 20 is connected to the antenna unit 10 and is configured to transmit and receive signals through the antenna unit 10. The channel transceiver 20 is implemented in a form of being connected to each antenna, and here, the channel transceiver 20 is four channel transceivers 21 to 24 that are connected to each of antennas 11 to 14 of the antenna unit 10, but the present disclosure is not limited thereto. Each channel transceiver 21 to 24 adjusts the intensity and phase of a signal transmitted through the corresponding channel, and specifically, adjusts intensity and phase of a radio signal (e.g., a microwave signal) according to the values of intensity and phase allocated by the controller 80.

The signal generator 30 is configured to generate a signal according to the power supply. The transmission signal distributor 40 is configured to distribute a signal, and specifically, distributes the generated signal to each channel transceiver 21 to 24.

The reception channel selector 50 is connected to the channel transceiver 20 and is configured to select one of the channel transceivers 21 to 24 and output a signal received through the corresponding channel. The reception channel selector 50 may be formed of a switch.

The reception signal distributor 60 is configured to provide a signal received through an arbitrary antenna to the detector 70 by controlling the selection operation, i.e., the switching operation, of the reception channel selector 50.

The detector 70 is configured to detect the intensity and phase of a signal provided through the reception signal distributor 60. This detector 70 includes a microwave intensity detector 71 and a microwave phase detector 72 as shown in FIG. 3.

The controller 80 is configured to adjust the intensity and phase of a microwave signal transmitted through the antenna unit 10. In particular, the controller 80 assigns the values of intensity and phase calculated for thermal diffusion to the channel transceiver 20, and also according to the amount of change based on the intensity and phase of the signal detected by the detector 70, to control the channel transceiver 20 to adjust the intensity and phase of the transmitted signal.

The detailed connection relationship and structure between each component constituting the microwave heat spread apparatus 1 according to the embodiment of the present disclosure are shown in FIG. 3.

Each antenna 11 to 14 of the microwave heat spread apparatus 1 may be attached to, for example, an affected part of the human body 2 (see FIG. 1). For example, the antennas 11 to 14 may be arranged in a circular shape based on the affected part of the human body 2.

The signal generator 30 is connected to the transmission signal distributor 40, and the transmission signal distributor 40 is respectively connected to four channel transceivers 21 to 24, and also connected to the microwave intensity detector 71 and the microwave phase detector 72, respectively. The reception channel selector 50 is respectively connected to the channel transceivers 21 to 24, the reception signal distributor 60 is connected to the reception channel selector 50, and the reception signal distributor 60 is also connected to the detector 71 and a microwave phase detector 72, respectively. The microwave intensity detector 71 and the microwave phase detector 72 are connected to the controller 80. The controller 80 is connected to the channel transceivers 21 to 24, respectively.

Meanwhile, each channel transceiver has the following structure.

Figure 4:
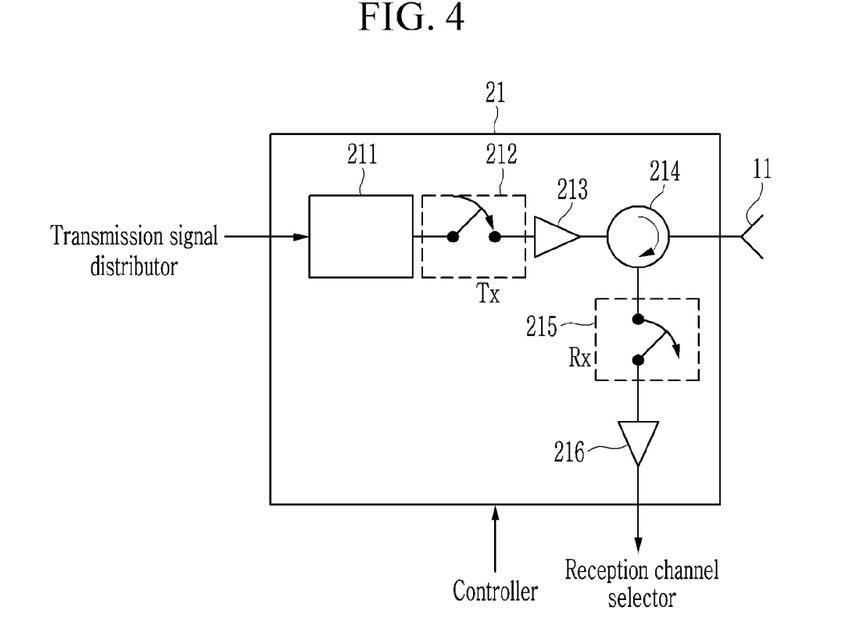
FIG. 4 is a diagram illustrating a detailed structure of a channel transceiver according to an embodiment of the present disclosure.

FIG. 4 is a diagram illustrating a detailed structure of a channel transceiver according to an embodiment of the present disclosure.

Here, the structure will be described using one channel transceiver 21 among the plurality of channel transceivers as an example, and the same structure may be applied to other channel transceivers 22 to 24.

One channel transceiver 21, as shown in FIG. 4, includes a microwave intensity and phase controller 211, a transmitting switch 212, a transmission amplifier 213, a circulator 214, a receiving switch 215, and a reception amplifier 216.

The microwave intensity and phase controller 211 is configured to adjust the intensity and phase of the signal provided from the transmission signal distributor 40 according to the values of intensity and phase applied from the controller 80.

The transmitting switch 212 is connected to the output terminal of the microwave intensity and phase controller 211, and is configured to be turned on/off according to a control signal from the controller 80 to send the signal output from the microwave intensity and phase controller 211 to the transmission amplifier 213.

The transmission amplifier 213 is connected to the output terminal of the transmitting switch 212 and is configured to send an applied signal to the circulator 214.

The circulator 214 is formed between the transmission amplifier 213 and the antenna 11, and is configured to send a signal from the amplifier 213 to the antenna 11, or send a signal from the antenna 11 to the receiving switch 215.

The receiving switch 215 is connected to the output terminal of the circulator 214, and is configured to be turned on/off according to a control signal applied from the controller 80 to send a signal received by the antenna 11 to the reception amplifier 216.

The reception amplifier 216 is configured to amplify the received signal and output it to the reception channel selector 50.

The other channel transceivers 22 to 24 also include a microwave intensity and phase controller, a transmitting switch, a transmission amplifier, a circulator, a receiving switch, and a reception amplifier, respectively, as described above.

In the microwave heat spread apparatus 1 according to the embodiment of the present disclosure having such a structure, the transmission operation is performed as follows.

The signal generated by the signal generator 30 is distributed by the transmission signal distributor 40 and sent to each of the four channel transceivers 21 to 24. The sent signal is adjusted in intensity and phase by the microwave intensity and phase controller 211 of the corresponding channel transceiver (e.g., 21). The microwave intensity and phase controller 211 adjusts the intensity and phase of the signal inputted from the transmission signal distributor 40 according to the values of intensity and phase allocated for thermal diffusion by the controller 80 and then outputs them. The signal whose intensity and phase are adjusted is amplified in the transmission amplifier 213 through the transmitting switch 212, and then radiated inside the human body 2 with the affected part through the antenna 11 via the circulator 214. As heat is generated by the signal transmitted through this process, that is, the signal radiated inside the human body 2, treatment for the affected part can be performed.

Next, the operation of detecting a change in body temperature may be performed as follows. For example, when a predetermined time elapses after the above transmission operation is performed, the operation of detecting a change in body temperature may be performed.

When the operation of detecting a change in body temperature is performed, the transmission operation is performed only through one antenna among the plurality of antennas and the reception operation is performed through the other antennas. To this end, only the transmitting switch of the channel transceiver (e.g., 21) connected to the antenna on which the transmission operation is performed is turned on, and the transmitting switch of the remaining channel transceivers (e.g., 22 to 24) is turned off. In addition, the receiving switch of the channel transceiver 21 is turned off, and the receiving switches of the remaining channel transceivers 22 to 24 are turned on to perform a reception operation.

Accordingly, the signal generated by the signal generator 30 and distributed by the transmission signal distributor 40 is radiated and propagated into the human body 2 through one channel transceiver 21, and the radio signals (S1 to S3 in FIG. 4) that have been passed through the human body 2 are received through the remaining channel transceivers 21 to 24. Accordingly, the signal received by each of the channel transceivers 22 to 24 is output via a circulator, a receiving switch, and a reception amplifier.

In this way, the received signal output from each of the channel transceivers 22 to 24 is distributed to the reception signal distributor 60 by the reception channel selector 50. The reception channel selector 50 may send the received signals output from the channel transceivers 22 to 24 to the reception signal distributor 60 by sequentially selecting or randomly selecting the received signals.

The reception signal distributor 60 sends the received signals to the microwave intensity detector 71 and the microwave phase detector 72, respectively.

The microwave intensity detector 71 detects the microwave intensity of the received signal, and in particular, compares the microwave intensity before passing through the human body with the microwave intensity after passing through the human body to detect an amount of change in the microwave intensity $|S_{21}|$. That is, the microwave intensity detector 71 compares the microwave intensity before passing through the human body, which is the intensity of the signal input from the transmission signal distributor 40, and the microwave intensity after passing through the human body, which is the intensity of the signal input from the receive signal splitter 60, to detect the amount of change in the microwave intensity, and sends it to the controller 80.

The microwave phase detector 72 detects the phase of the received signal, and in particular, compares the phase before passing through the human body with the microwave phase after passing through the human body to detect an amount of change in the microwave phase $\angle S_{21}$. That is, the microwave phase detector 72 compares the microwave phase before passing through the human body, which is the phase of the signal input from the transmission signal distributor 40, and the microwave phase after passing through the human body, which is the intensity of the signal input from the receive signal splitter 60, to detect the amount of change in the microwave phase, and then sends it to the controller 80.

The controller 80 estimates the amount of change in body temperature based on the amount of change in the microwave intensity and the amount of change in the microwave phase.

For example, if the microwave intensity M and the microwave phase θ are first measured at a time t1, the dielectric constant $\epsilon'$ and conductivity σ of the entire medium along the path through which the microwave has passed can be obtained as follows.

$$M(\epsilon', \sigma) = G_t + G_r - 20\log_{10}^{2\beta d} - 20ad\log_{10}^{e} \text{ [dB]} \quad \text{Equation 1}$$

$$\theta(\epsilon', \sigma) = -57.296\beta d \text{ [deg]}$$

$$\alpha = \omega\sqrt{\mu\epsilon'}\sqrt{\frac{1}{2}\left[\sqrt{1+\left(\frac{\sigma}{\omega\epsilon'}\right)^2}-1\right]} \text{ [Np/m]}$$

$$\beta = \omega\sqrt{\mu\epsilon'}\sqrt{\frac{1}{2}\left[\sqrt{1+\left(\frac{\sigma}{\omega\epsilon'}\right)^2}+1\right]} \text{ [rad/m]}$$

In this way, when the dielectric constant $\epsilon'$ and conductivity σ are obtained, the temperature T of the entire medium can be obtained as follows.

$$\epsilon'(T) = \epsilon_o\left\{\epsilon_\infty + \frac{\epsilon_s - \epsilon_\infty}{1+\omega^2\tau_o^2\left[\exp\left(\frac{E_a}{RT}\right)\right]^2}\right\} \quad \text{Equation 2}$$

$$\sigma(T) = \frac{1}{\rho_o\exp\left(\frac{E_g}{kT}\right)+\rho_o\exp\left(\sqrt{\frac{T_o}{T}}\right)}$$

In the above Equation 2, G represents the antenna gain, d represents the path distance of microwaves, μ represents the transmittance of the medium, and ω represents each frequency according to the microwave frequency, which may be a fixed constant by the apparatus.

In this way, after obtaining the temperature T at the time t1, the above process (the process of obtaining the dielectric constant $\epsilon'$ and the conductivity σ and then obtaining the temperature T based on Equations 1 and 2) is repeatedly performed for a second time t2 to obtain the temperature T, and the amount of change in body temperature can be estimated based on the difference between the obtained temperatures.

The estimated amount of change in body temperature is compared with a predetermined threshold. If the amount of change in body temperature exceeds the threshold, the microwave heat generating operation is stopped, and if the amount of change in body temperature does not exceed the threshold, the microwave heat generating operation continues.

Figure 5:
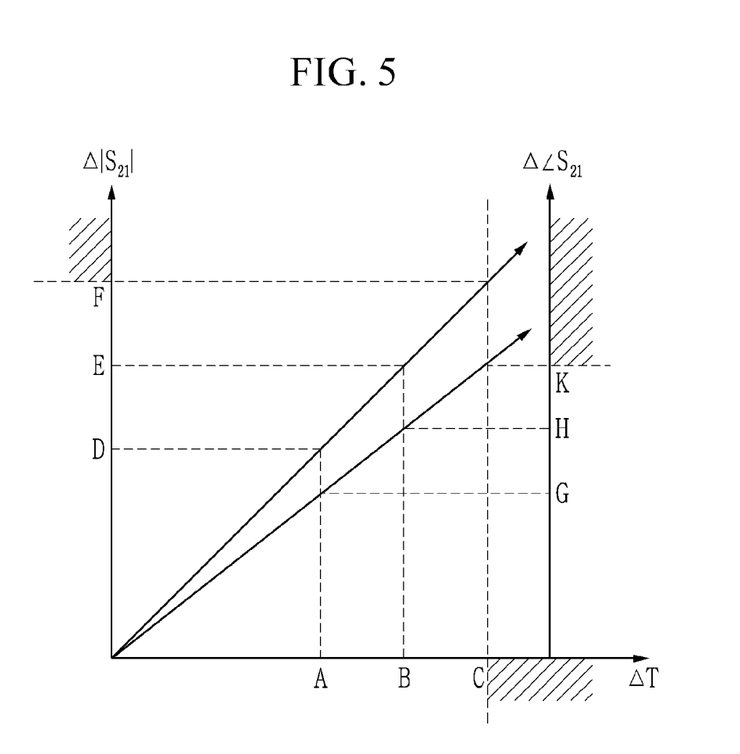
FIG. 5 is a graph illustrating a relationship between a temperature change amount and a threshold according to an embodiment of the present disclosure.

FIG. 5 is a graph illustrating a relationship between a temperature change amount and a threshold according to an embodiment of the present disclosure.

As shown in FIG. 5, the amount of change in body temperature A, D, G or B, E, H is detected based on the amount of change in the microwave intensity $\angle S_{21}$ and the amount of change in the microwave phase $\angle S_{21}$. If this amount of change in body temperature exceeds the thresholds C, F, or K at which there is a risk of tissue destruction due to generation of high heat during the treatment, the channel transceivers 21 to 24 are controlled (for example, by turning off the transmitting switch to avoid microwave radiation) to stop the microwave heat generating operation until the amount of change in body temperature becomes lower than the threshold.

Next, an operating method of the microwave heat spread apparatus according to an embodiment of the present disclosure will be described based on this structure.

Figure 6:
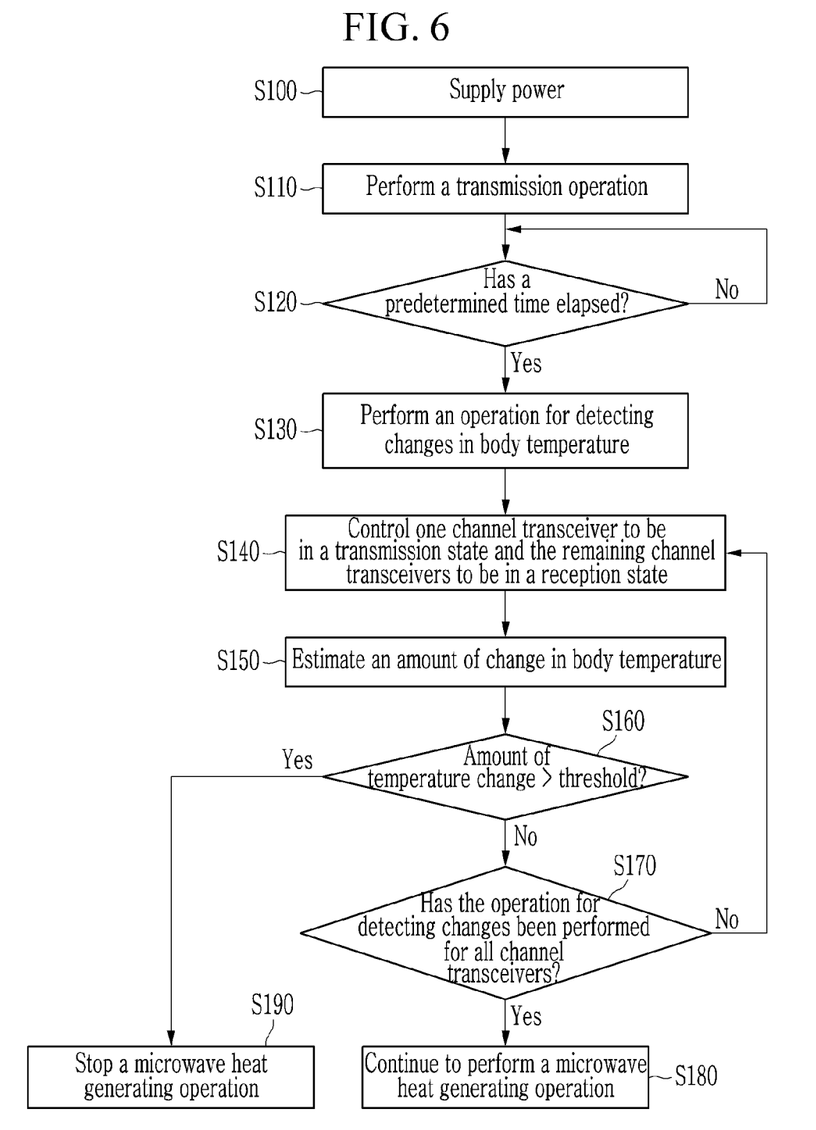
FIG. 6 is a flowchart of a method of operating a microwave heat spread apparatus according to an embodiment of the present disclosure.
Figure 7:
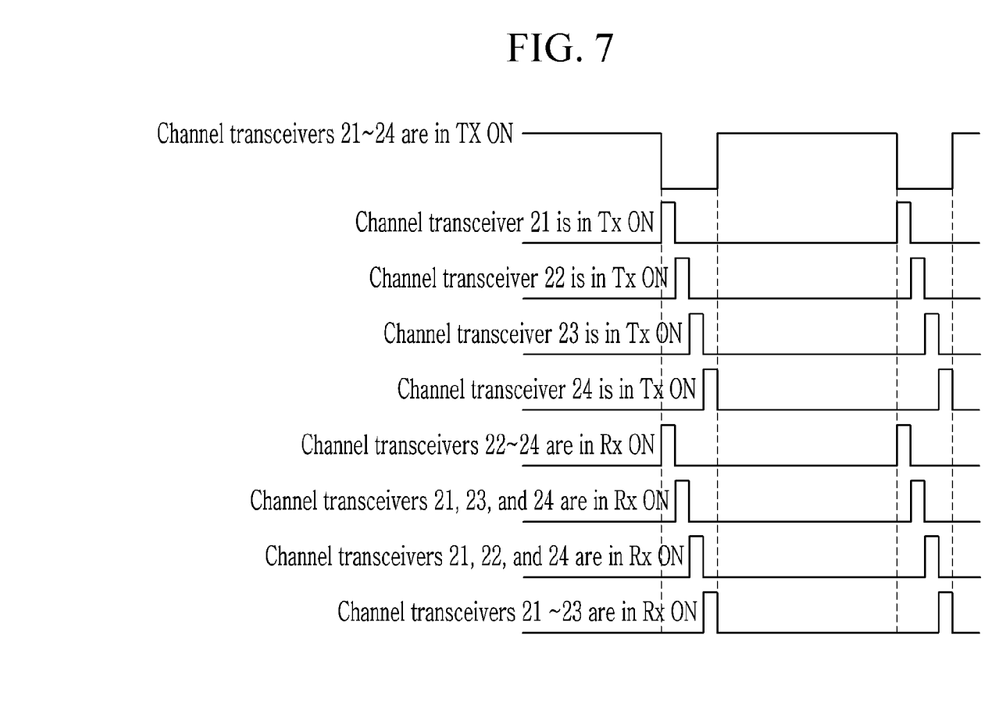
FIG. 7 is an operation timing diagram of a microwave heat spread apparatus according to an embodiment of the present disclosure.

FIG. 6 is a flowchart of a method of operating a microwave heat spread apparatus according to an embodiment of the present disclosure. FIG. 7 is an operation timing diagram of a microwave heat spread apparatus according to an embodiment of the present disclosure.

As shown in FIG. 6, the microwave heat spread apparatus 1 performs a microwave heat generating operation when power is applied. To this end, first, as shown in FIG. 7, the transmitting switches Tx of all the channel transceivers 21 to 24 are turned on so that microwaves are radiated into the human body through all the antennas 11 to 14 (S100, S110). Accordingly, the four channel transceivers 21 to 24 are simultaneously in the transmission state (Tx ON) so that thermal treatment is performed.

Thereafter, for example, when a predetermined time elapses (S120), an operation for detecting changes in body temperature is performed (S130). To this end, only one channel transceiver among the four channel transceivers 21 to 24 performs a transmission operation and the remaining channel transceivers are controlled to perform a reception operation (S140).

Specifically, as shown in FIG. 7, only one channel transceiver 21 is in the transmission state (Tx ON) and the remaining channel transceivers 22 to 24 are in the reception state (Rx ON) for a certain period of time. Then, the amount of change in body temperature (may also be referred to as the amount of temperature change for convenience of explanation) is estimated based on the received signal (S150). By comparing the amount of temperature change and the threshold (S160), if the amount of temperature change does not exceed the threshold, another channel transceiver (e.g., 22) is put into the transmission state (Tx ON), and the remaining channel transceivers (e.g., 21, 23, and 24) are put into the reception state (Rx ON), and then the amount of temperature change is again estimated and compared with the threshold. This operation is repeatedly performed for all the channel transceivers 21 to 24 in a state in which the amount of temperature change does not exceed the threshold (S170).

For example, as in FIG. 7, sequentially, a process in which only the channel transceiver 22 is in the transmission state (Tx ON) while the remaining channel transceivers 21, 23, and 24 are in the reception state (Rx ON), a process in which only the channel transceiver 23 is in the transmission state (Tx ON) while the remaining channel transceivers 21, 22, and 24 are in the reception state (Rx ON), a process in which only the channel transceiver 24 is in the transmission state (Tx ON) while the remaining channel transceivers 21 to 23 are in the reception state (Rx ON), are performed, respectively. In performing each process, the amount of temperature change is estimated as described above, and if the amount of temperature change does not exceed the threshold, the following process is performed.

When the operation of detecting a change in body temperature is completed for all the channel transceivers 21 to 24, the microwave heat generating operation is continued (S180). That is, as in step S110, all the channel transceivers 21 to 24 are put into the transmission state so that the heat treatment in which microwaves are radiated into the human body is performed.

On the other hand, when the amount of temperature change estimated in the transmission state for each channel transceiver exceeds the threshold, the microwave heat generating operation is terminated (S190).

Meanwhile, in the above embodiment, only one channel transmitter among the plurality of channel transceivers operates in the transmission state and all the other channel transceivers operate in the reception state as an example, but there may be at least one channel transceiver operating in the reception state. For example, the operation of detecting a change in body temperature as described above may be performed while only one channel transmitter among the plurality of channel transceivers operates in a transmission state and only one channel transceiver among the remaining channel transceivers operates in a reception state.

According to this embodiment of the present disclosure, by controlling the generation of microwave heat by estimating the amount of change in body temperature in the transmission state for each channel transceiver, it is possible to easily estimate the amount of change in body temperature at various locations in the human body, and based on the estimation result, by controlling heat generation, accidents due to overheating in a specific location can be prevented in advance.

Figure 8:
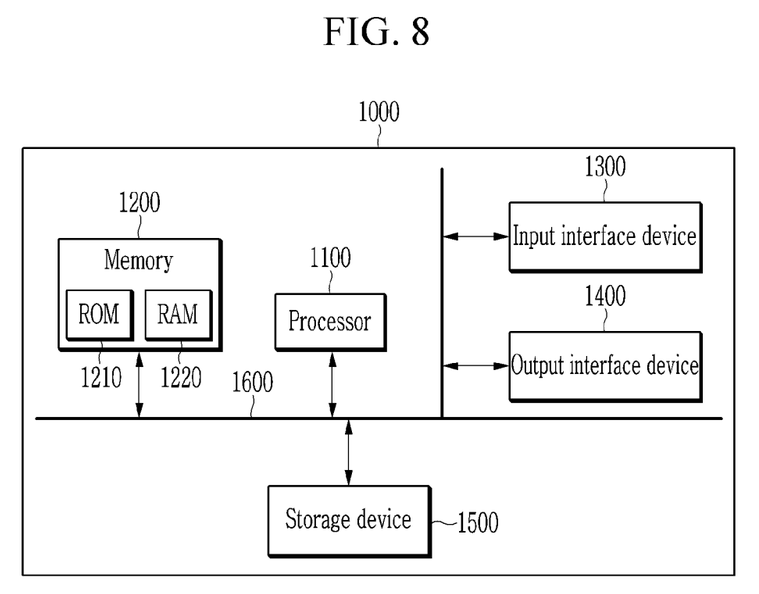
FIG. 8 is a structural diagram illustrating a computing device for implementing an operating method according to an embodiment of the present disclosure.

FIG. 8 is a structural diagram illustrating a computing device for implementing an operating method according to an embodiment of the present disclosure.

As illustrated in FIG. 8, the operating method according to an embodiment of the present disclosure may be implemented using the computing device 1000.

The computing device 1000 may include at least one of a processor 1100, a memory 1200, an input interface device 1300, an output interface device 1400, and a storage device 1500. Each of the components may be connected by a bus 1600 to communicate with each other. In addition, each of the components may be connected through an individual interface or a separate bus with the processor 1100 as the center instead of the common bus 1600.

The processor 1100 may be implemented as various types such as an application processor (AP), a central processing unit (CPU), a graphics processing unit (GPU), and the like, and may be any semiconductor device that executes an instruction stored in the memory 1200 or the storage device 1500.

The processor 1100 may execute a program command stored in at least one of the memory 1200 and the storage device 1500. The processor 1100 may be configured to implement the functions and methods described based on FIGS. 6 and 7 above. For example, the processor 1100 may be configured to the function of the controller 80. In addition, the processor 1100 may communicate with another processor through the bus 1600.

The memory 1200 and the storage device 1500 may include various types of volatile or non-volatile storage media. For example, the memory may include a read-only memory (ROM) 1210 and a random access memory (RAM) 1220. In an embodiment of the present disclosure, the memory 1200 may be located inside or outside the processor 1100, and the memory 1200 may be connected to the processor 1100 through various known means.

The input interface device 1300 is configured to provide data to the processor 1100, and the output interface device 1400 is configured to output data from the processor 1100.

The computing device 1000 having such a structure is called a microwave heat spread apparatus, and may implement the operation method according to an embodiment of the present disclosure.

In addition, at least a part of the phase information processing method according to an embodiment of the present disclosure may be implemented as a program or software executed in the computing device 1000, and the program or software may be stored in a computer-readable medium.

In addition, at least a part of the phase information processing method according to an embodiment of the present disclosure may be implemented as hardware capable of being electrically connected to the computing device 1000.

According to the embodiments, heat by using microwaves is generated in the human body and the heat is spread to be uniformly distributed. In particular, the amount of temperature change is predicted based on the amount of change in the intensity and phase of the microwaves passing through the body tissue to easily control the operation of generating microwave heat.

In particular, it is possible to transmit microwaves into the human body and receive them from the opposite side, compare the intensity of the transmitted microwaves with the intensity of the received microwaves to detect the microwave change amount, and estimate the amount of temperature change from the microwave change amount. In addition, since the microwave change amount detection and temperature change amount estimation can be performed for each channel transmitter corresponding to each of the plurality of antennas, it is possible to easily estimate the amount of temperature change at various locations, particularly, at various locations in affected areas of the human body.

In addition, if the amount of temperature change is equal to or greater than the threshold, the generation of heat may be stopped, and if the amount of temperature change is equal to or less than the threshold, the generation of heat may be continued.

In addition, path separation is made between the high-power transmitting means for transmitting microwaves and the receiving means for receiving microwaves by using a circulator in the thermal diffusion.

Accordingly, it is possible to non-invasively detect changes in body temperature and, based on this information, prevent in advance the risk of tissue destruction due to high heat generation in non-invasive treatment of diseases such as pain disorders and degenerative musculoskeletal diseases.

The apparatus and method according to an embodiment of the present disclosure may be applied to various microwave heat hyperthermia apparatuses.

The embodiments of the present disclosure are not implemented only through the apparatus and/or method described above, but may be implemented through a program for realizing a function corresponding to the configuration of the embodiment of the present disclosure, and a recording medium in which the program is recorded. This implementation can also be easily performed by expert person skilled in the technical field to which the present disclosure belongs from the description of the above-described embodiments.

The components described in the embodiment s may be implemented by hardware components including, for example, at least one digital signal processor (DSP), a processor, a controller, an application-specific integrated circuit (ASIC), a programmable logic element such as an FPGA, other electronic devices, or combinations thereof. At least some of the functions or the processes described in the embodiment s may be implemented by software, and the software may be recorded on a recording medium. The components, functions, and processes described in the embodiment s may be implemented by a combination of hardware and software.

The method according to embodiment s may be embodied as a program that is executable by a computer, and may be implemented as various recording media such as a magnetic storage medium, an optical reading medium, and a digital storage medium. Various techniques described herein may be implemented as digital electronic circuitry, or as computer hardware, firmware, software, or combinations thereof. The techniques may be implemented as a computer program product, i.e., a computer program tangibly embodied in an information carrier, e.g., in a machine-readable storage device (for example, a computer-readable medium) or in a propagated signal for processing by, or to control an operation of a data processing apparatus, e.g., a programmable processor, a computer, or multiple computers. A computer program(s) may be written in any form of a programming language, including compiled or interpreted languages, and may be deployed in any form including a stand-alone program or a module, a component, a subroutine, or other units appropriate for use in a computing environment. A computer program may be deployed to be executed on one computer or on multiple computers at one site or distributed across multiple sites and interconnected by a communication network. Processors appropriate for execution of a computer program include, by way of example, both general and special purpose microprocessors, and any one or more processors of any kind of digital computer. Generally, a processor will receive instructions and data from a read-only memory or a random access memory or both. Elements of a computer may include at least one processor to execute instructions and one or more memory devices to store instructions and data. Generally, a computer will also include or be coupled to receive data from, transfer data to, or perform both on one or more mass storage devices to store data, e.g., magnetic disks, magneto-optical disks, or optical disks. Examples of information carriers appropriate for embodying computer program instructions and data include semiconductor memory devices, for example, magnetic media such as a hard disk, a floppy disk, and a magnetic tape, optical media such as a compact disk read only memory (CD-ROM), a digital video disk (DVD), etc., and magneto-optical media such as a floptical disk, and a read only memory (ROM), a random access memory (RAM), a flash memory, an erasable programmable ROM (EPROM), and an electrically erasable programmable ROM (EEPROM), and any other known computer readable medium. A processor and a memory may be supplemented by, or integrated with, a special purpose logic circuit. The processor may run an operating system (OS) and one or more software applications that run on the OS. The processor device also may access, store, manipulate, process, and create data in response to execution of the software. For the purpose of simplicity, the description of a processor device is used as singular, however, one skilled in the art will appreciate that a processor device may include multiple processing elements and/or multiple types of processing elements. For example, a processor device may include multiple processors or a processor and a controller. In addition, different processing configurations are possible, such as parallel processors. Also, non-transitory computer-readable media may be any available media that may be accessed by a computer, and may include both computer storage media and transmission media. The present specification includes details of a number of specific implementations, but it should be understood that the details do not limit any disclosure or what is claimable in the specification but rather describe features of the specific embodiment. Features described in the specification in the context of individual embodiment s may be implemented as a combination in a single embodiment. In contrast, various features described in the specification in the context of a single embodiment may be implemented in multiple embodiment s individually or in an appropriate sub-combination. Furthermore, the features may operate in a specific combination and may be initially described as claimed in the combination, but one or more features may be excluded from the claimed combination in some cases, and the claimed combination may be changed into a sub-combination or a modification of a sub-combination. Similarly, even though operations are described in a specific order in the drawings, it should not be understood that the operations needing to be performed in the specific order or in sequence to obtain desired results or as all the operations needing to be performed. In a specific case, multitasking and parallel processing may be advantageous. In addition, it should not be understood as requiring a separation of various apparatus components in the above-described embodiment s in all embodiment s, and it should be understood that the above-described program components and apparatuses may be incorporated into a single software product or may be packaged in multiple software products. It should be understood that the embodiment s disclosed herein are merely illustrative and are not intended to limit the scope of the disclosure. It will be apparent to one of ordinary skill in the art that various modifications of the embodiment s may be made without departing from the spirit and scope of the claims and their equivalents.

What is claimed is:

1. An apparatus for spreading microwave heat into a human body, comprising:
a plurality of antennas configured to be respectively disposed at a plurality of positions of the human body and radiating microwaves into the human body;

a plurality of channel transceivers respectively connected to the plurality of antennas and configured to transmit and receive the microwaves through a corresponding antenna;

a transmission signal distributor configured to distribute a signal to each of the plurality of channel transceivers;

a controller configured to control transmission and reception of signals through the channel transceivers; and a detector configured to detect a difference between a signal received through a channel transceiver after passing through the human body and a signal before passing through the human body, wherein in a state in which one channel transceiver of the plurality of channel transceivers operates in a transmission state and at least one of remaining channel transceivers operates in a reception state, the controller estimates an amount of temperature change based on the difference output from the detector and controls the channel transceivers according to the estimated amount of temperature change;

wherein the detector uses a signal provided from the transmission signal distributor as the signal before passing through the human body, and the detector includes:

a first detector configured to detect an intensity difference between an intensity of a signal received through the channel transceiver and an intensity of a signal provided from the transmission signal distributor; and a second detector configured to detect a phase difference between a phase of a signal received through the channel transceiver and a phase of a signal provided from the transmission signal distributor, wherein the controller is configured to estimate the amount of temperature change in the human body based on the intensity difference and the phase difference.

2. The apparatus of claim 1, wherein
the controller is configured to control the plurality of channel transceivers to stop a microwave heat generating operation for radiating microwaves through the plurality of antennas when the estimated amount of temperature change exceeds a predetermined threshold, and control the plurality of channel transceivers to continue the microwave heat generating operation when the estimated amount of temperature does not exceed the predetermined threshold.

3. The apparatus of claim 1, wherein
for each of the plurality of channel transceivers, the estimating of the amount of temperature change is performed while a corresponding channel transceiver operates in a transmission state and at least one of the remaining channel transceivers operates in a reception state.

4. The apparatus of claim 1, wherein
the controller is configured to perform first control of controlling all of the plurality of channel transceivers to be in a transmission state so that a microwave heat generating operation in which microwaves are radiated through all of the antennas respectively connected to the plurality of channel transceivers is performed, and when a predetermined time elapses after performing the first control, perform second control of controlling one channel transceiver among the plurality of channel transceivers to be in a transmission state and controlling at least one of the remaining channel transceivers to be in a reception state.

5. The apparatus of claim 4, wherein
the controller is configured to repeatedly perform the second control while operating each of the plurality of channel transceivers in a transmission state, and perform the operation of estimating the amount of temperature change based on the intensity difference and phase difference from the detector and comparing the estimated amount of temperature change with a predetermined threshold whenever the second control is performed.

6. The apparatus of claim 1, wherein
each of the plurality of channel transceivers includes:
a transmitting switch;
a circulator configured to send a signal from the transmitting switch to a corresponding antenna so that microwave radiation is performed or to output a signal received from the corresponding antenna; and
a receiving switch connected to an output terminal of the circulator and configured to be turned on/off according to a control signal applied from the controller to send the received signal output from the circulator to the detector,
wherein a transmission operation is performed through the corresponding antenna according to on/off of the transmitting switch, and a reception operation is performed through the corresponding antenna according to on/off of the receiving switch.

7. The apparatus of claim 6, wherein
each of the plurality of channel transceivers includes:
a microwave intensity and phase controller configured to adjust an intensity and phase of a signal provided from the transmission signal distributor according to values of intensity and phase provided from the controller and output to the transmitting switch;
a transmission amplifier configured to amplify a signal applied through the transmitting switch and send it to the circulator; and
a reception amplifier configured to amplify a signal applied through the receiving switch and send it to the detector.

8. The apparatus of claim 1, further comprising:
a reception channel selector connected to an output terminal of the plurality of channel transceivers and configured to select a single channel transceiver; and
a reception signal distributor connected to an output terminal of the reception channel selector to transmit a signal output from the reception channel selector to the detector.

9. The apparatus of claim 1, wherein
each of the plurality of antennas is an antenna configured to be attached to the human body via a cable, and the apparatus operates as a non-invasive microwave hyperthermia apparatus.

* * * * *